United States Patent
Lu et al.

(10) Patent No.: US 11,649,244 B2
(45) Date of Patent: May 16, 2023

(54) METHOD FOR SYNTHESIZING DIAZA-BRIDGED COMPOUND AND A DIAZA-BRIDGED COMPOUND

(71) Applicant: LinkChem Co., Ltd., Shanghai, Shanghai (CN)

(72) Inventors: Xi Lu, Shanghai (CN); Shuai Liu, Shanghai (CN); Yong Liang, Shanghai (CN); Jiaming Cai, Shanghai (CN); Quan Tang, Shanghai (CN); Yuan Zeng, Shanghai (CN)

(73) Assignee: LINKCHEM CO., LTD., SHANGHAI, Shanghai (CN)

( * ) Notice: Subject to any disclaimer, the term of this patent is extended or adjusted under 35 U.S.C. 154(b) by 0 days.

(21) Appl. No.: 17/564,864

(22) Filed: Dec. 29, 2021

(65) Prior Publication Data
US 2022/0119397 A1    Apr. 21, 2022

(30) Foreign Application Priority Data

Jul. 14, 2021  (CN) ......................... 202110793773.X
Aug. 10, 2021  (CN) ......................... 202110912395.2

(51) Int. Cl.
C07D 487/08   (2006.01)
C07D 205/04   (2006.01)

(52) U.S. Cl.
CPC ......... *C07D 487/08* (2013.01); *C07D 205/04* (2013.01)

(58) Field of Classification Search
CPC ........................... C07D 487/08; C07D 205/04
See application file for complete search history.

(56) References Cited

PUBLICATIONS

Chemical Abstracts Registry Nos. 2749519-62-6, 2749519-61-5, 2749519-59-1, indexed in the Registry file on ACS on STN, Dec. 17, 2021.*

* cited by examiner

*Primary Examiner* — Rebecca L Anderson
(74) *Attorney, Agent, or Firm* — IPro, PLLC

(57) ABSTRACT

The present disclosure discloses a method for synthesizing a diaza-bridged compound and a diaza-bridged compound, belonging to the field of organic synthesis. The present disclosure includes the following reaction:

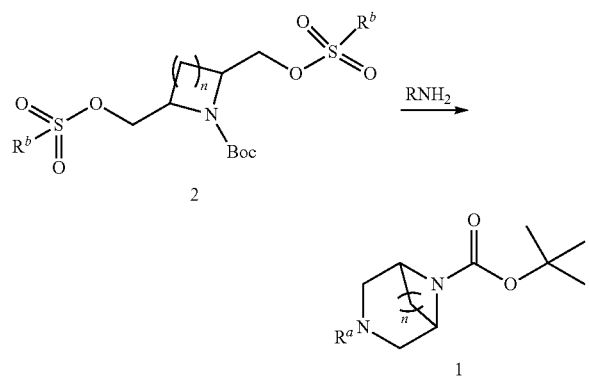

in the formula, R is aryl, substituted aryl, alkyl or haloalkyl, $R^a$ is any one of H, 2-nitrobenzenesulfonyl, 4-nitrobenzenesulfonyl or 2,4-dinitrobenzenesulfonyl, n=1 or 2. Since compound 2 and $NH_3$ are used as raw materials, the present disclosure can not only effectively shorten the process flow and save process costs, but also improve the reaction yield to a certain extent. The present disclosure also provides a diaza-bridged compound, where the structural formula thereof is

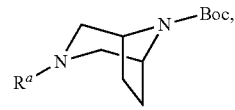

in the formula, $R^a$ is any one of 2-nitrobenzenesulfonyl, 4-nitrobenzenesulfonyl or 2,4-dinitrobenzenesulfonyl. Since the compound has a higher melting point, is easy to recrystallize to get solid and not easy to form oil under high temperature, the diaza-bridged compound is suitable for long-distance transportation and long-term storage.

4 Claims, 5 Drawing Sheets

METHOD FOR SYNTHESIZING DIAZA-BRIDGED COMPOUND AND A DIAZA-BRIDGED COMPOUND

TECHNICAL FIELD

The disclosure relates to a method for synthesizing a diaza-bridged compound and a diaza-bridged compound, belonging to the field of organic chemistry.

BACKGROUND

Diaza-bridged compound is a very useful pharmaceutical intermediate. There are a large number of medicines with diaza-bridged fragments, such as Selpercatinib (Compound I) for the treatment of rearranged during transfection fusion-positive metastatic non-small cell lung cancer developed by Eli Lilly and Company in the United States, a retinoic acid-related orphan nuclear receptor modulator (Compound II) developed by Escalier in the United States, a medicine (Compound III) for inhibiting type I 11β-hydroxysteroid dehydrogenase developed by Schering in the United States and Brepocitinib (Compound IV) for the treatment of various immune diseases developed by Pfizer in the United States, etc.

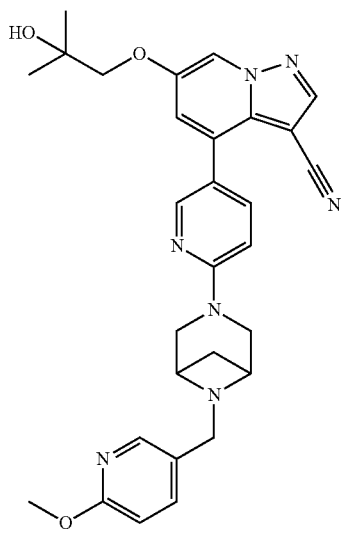

Compound I

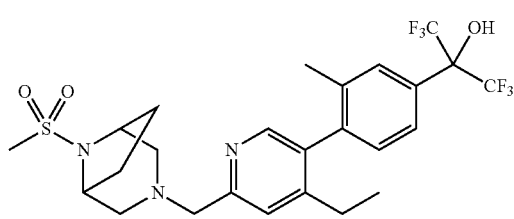

Compound II

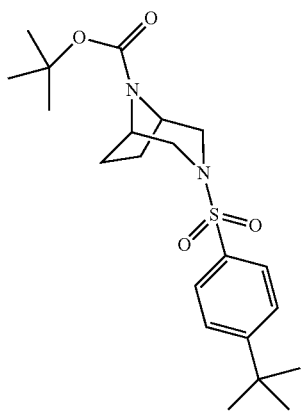

Compound III

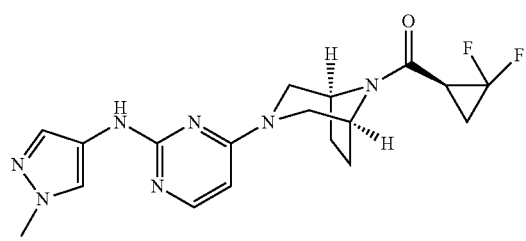

Compound IV

It is reported that the synthesis procedure for the above-mentioned medicines are directly or indirectly involved in compound 1a or 1b.

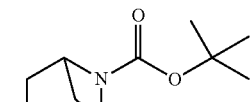

compound 1a

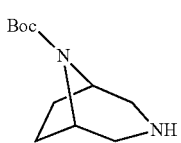

compound 1b

The method for synthesizing compound 1a in the art is as follows:

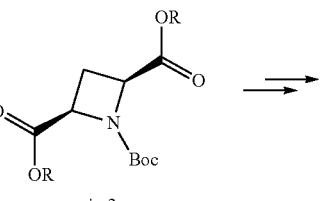

cis-2

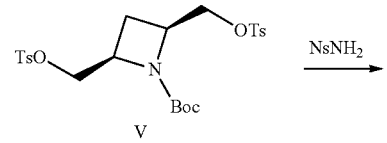

V

-continued

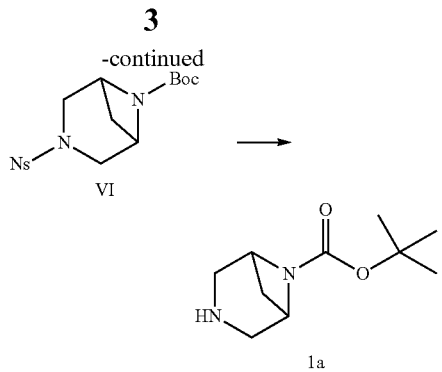

From the above reaction route, it can be seen that two steps are required for converting compound V to compound 1a, and a large amount of o-nitrobenzenesulfonic acid will be additionally produced. The release of o-nitrotoluenesulfonic acid will not only bring trouble to the post-treatment of the reaction, but also make the entire reaction system acidic, which may cleave the tert-butyloxycarbonyl group and thus reduce the reaction yield.

Further, in the above route, compound cis-2 is used as the starting material, but it will produce a large amount of trans-byproducts during the synthesis process with a cis/trans ratio of about 1:1, which obviously results in lower yield. Since the products have lower cis/trans ratio, the cis and trans products are required to be subsequently analyzed by column chromatography, which also makes it difficult for compound 1a to achieve an industrial production.

The method for synthesizing compound 1b in the art is as follows:

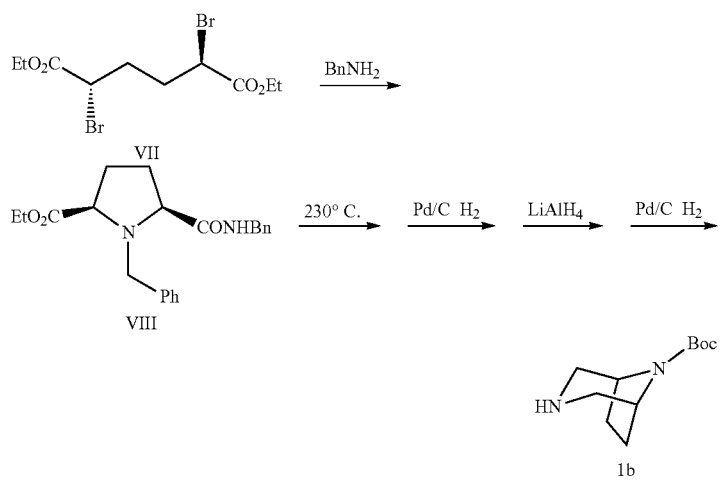

It can be seen from the above route that during the synthesis of compound 1b, it is not only necessary to go through harsher reaction conditions such as a temperature as high as 230° C., but also to repeatedly use reducing reagents such as Pd/C for reduction. The entire synthetic route is relatively long. The actual production process is not economical and environmentally friendly. In addition, this route also has certain requirements on the stereoconfiguration of the compound VII as an initial reaction substrate, which will further increase the production cost.

Further, since the melting point of pure compound 1b is only 58° C.-60° C., compound 1b will become a viscous oil if the storage temperature or transportation temperature is higher than 40° C. Once it becomes a viscous oil, even if the temperature is restored to room temperature, compound 1b will still maintain the oily state and will not recrystallize. Due to the above-mentioned characteristics of compound 1b, it is difficult for compound 1b to be stored and transported for a long time, and it is troublesome for compound 1b to be taken and weighed after forming an oil.

On the other hand, in the process of preparing compound 1b, the purity thereof must be increased to a higher level to finally obtain the crystals of compound 1b. In the prior art, in order to obtain the crystals of compound 1b, it is often necessary to be purified by column chromatography, which also increases the industrial production difficulty of compound 1b.

In addition, in the process of preparing medicines from compound 1b, it is sometimes necessary to firstly modify the N at position 8. In this case, it is necessary to firstly protect the N at position 3 of the compound 1b, then remove the Boc protecting group at position 8, and finally modify the N at position 8, which will result in a very cumbersome reaction process and a heavier workload.

SUMMARY

The present disclosure was made to solve the above-mentioned problems, and its purpose is to provide a method for synthesizing a diaza-bridged compound with simplified steps and high yield, and a multi-purpose diaza-bridged compound that has a higher melting point, is easy to store and transport, easy to purify, and can be efficiently applied to the synthesis of multiple medicines.

Unless otherwise specified, the following definitions as used herein shall apply. In addition, many of the groups defined herein can be optionally substituted. The enumeration of substituents in the definition is exemplary and should not be construed as limiting the substituents defined elsewhere in this specification.

As used herein, the term "alkyl" refers to a straight or branched hydrocarbon chain group consisting of only carbon atoms and hydrogen atoms that does not contain unsaturation, has one to ten carbon atoms and are attached to the rest of the molecule via single bonds, such as methyl, ethyl, n-propyl, 1-methylethyl (isopropyl), n-butyl, n-pentyl, and 1,1-dimethylethyl (tert-butyl). The term "C1-10 alkyl" refers to an alkyl group as defined above having up to 10 carbon atoms.

As used herein, the term "aryl" refers to an aromatic group with carbon atoms ranging from 6 to 20, such as phenyl, naphthyl, tetrahydronaphthyl, indanyl, biphenyl and the like.

As used herein, the term "substituted" refers to the substitution with any one or any combination of the following substituents which may be the same or different and are independently selected from alkyl, hydroxyl, halogen, carboxyl, cyano, and nitro, p-methylphenyl when referring to the term "substituted aryl", o-nitrophenyl when referring to the term "substituted aryl" and the like.

As used herein, the term "halo", "halide" or alternatively, "halogen" means fluorine, chlorine, bromine or iodine. The term "haloalkyl" refers to an alkyl group substituted with one or more halo groups or a combination thereof, such as trifluoromethyl and the like.

As used herein, the term "contact" should be understood in a broad sense, and it can be any means through which at least two reactants can undergo a chemical reaction, for example, a means through which two reactants are mixed under appropriate conditions. If necessary, the reactants that need to be contacted can be mixed under stirring. Therefore, the type of stirring is not particularly limited. For example, it can be mechanical stirring, i.e., stirring under the action of mechanical force.

The present disclosure provides a method for synthesizing a diaza-bridged compound which is used for preparing the compound

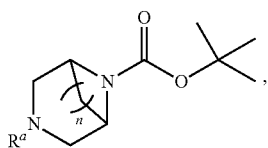

including the following reaction:

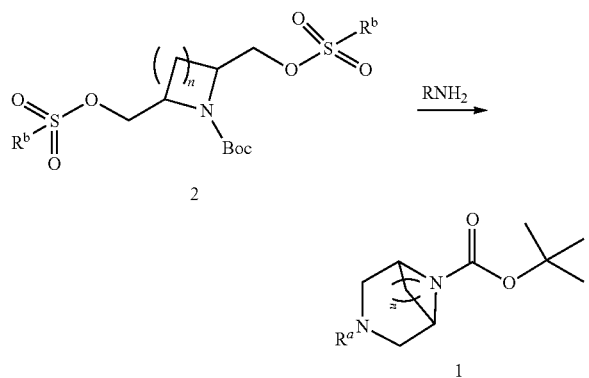

in the formula, $R^b$ is any one of aryl, substituted aryl, alkyl or haloalkyl, R is any one of H, 2-nitrobenzenesulfonyl, 4-nitrobenzenesulfonyl or 2,4-dinitrobenzenesulfonyl, n=1 or 2, and $R^a$ is any one of H, 2-nitrobenzenesulfonyl, 4-nitrobenzenesulfonyl or 2,4-dinitrobenzenesulfonyl; where,
when $R^b$ is aryl, substituted aryl, alkyl or haloalkyl, R is H, $R^a$ is H, and n=1 or 2, the reaction steps are as follows:

step 1 of contacting compound 2 with $NH_3$ or $NH_3$ solution to obtain a reaction mixture; and
step 2 of post-treatment the reaction mixture in step 1 to obtain compound 1;
when $R^b$ is methyl or p-tolyl, R is any one of 2-nitrobenzenesulfonyl, 4-nitrobenzenesulfonyl or 2,4-dinitrobenzenesulfonyl, $R^a$=R, and n=2, the reaction steps are as follows:
step a of contacting compound 2 with $R^aNH_2$ or $R^aNH_2$ solution to obtain a reaction mixture; and
step b of post-treatment the reaction mixture in step a to obtain compound 1;
when $R^b$ is methyl or p-tolyl, R is H, $R^a$ is any one of 2-nitrobenzenesulfonyl, 4-nitrobenzenesulfonyl or 2,4-dinitrobenzenesulfonyl, and n=2, the reaction steps are as follows: step i of contacting compound 2 with $NH_3$ or $NH_3$ solution to obtain a reaction mixture;
step ii of post-treatment the reaction mixture to obtain compound

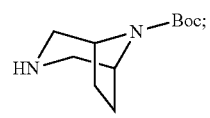

and
step iii of acylating the compound obtained in step ii with an acylation reagent to obtain compound 1, where the acylation reagent is $R^aX$ or $R^aOR^a$, in which X is chlorine or bromine.

The method for synthesizing a diaza-bridged compound provided in the present disclosure may also have the following characteristics that in step 1 or step i, compound 2 is contacted with $NH_3$ or $NH_3$ solution in a reaction medium.

The method for synthesizing a diaza-bridged compound provided in the present disclosure may also have the following characteristics that in step 1 or step i, the method for contacting compound 2 with $NH_3$ or $NH_3$ solution can be performed either by adding compound 2 or a solution thereof to $NH_3$ or a solution thereof, or by adding $NH_3$ or $NH_3$ solution to compound 2 or a solution thereof, where $NH_3$ or $NH_3$ solution can be ammonia, liquid ammonia, aqueous ammonia, or an organic solution of ammonia.

The method for synthesizing a diaza-bridged compound provided in the present disclosure may also have the following characteristics that in step 1 or step i, the reaction medium is a non-alcohol liquid.

The method for synthesizing a diaza-bridged compound provided in the present disclosure may also have the following characteristics that in step 1 or step i, the non-alcohol liquid is any one or more of water, acetonitrile, DMF or tetrahydrofuran.

The method for synthesizing a diaza-bridged compound provided in the present disclosure may also have the following characteristics that Rb in compound 2 is methyl or p-methylphenyl.

The method for synthesizing a diaza-bridged compound provided in the present disclosure may also have the following characteristics that in step 1 or step i, compound 2 is contacted with $NH_3$ or $NH_3$ solution in step 1 at 25° C.-80° C., preferably 30° C.-70° C.

The method for synthesizing a diaza-bridged compound provided in the present disclosure may also have the following characteristics that in step 1, the contact time is 5 h-24 h, preferably 8 h-16 h, more preferably 8 h, 9 h, 10 h, 11 h, or 12 h.

The method for synthesizing a diaza-bridged compound provided in the present disclosure may also have the following characteristics that in step 1 or step i, NH$_3$ solution is aqueous ammonia with a concentration of 15 wt %-35 wt %, preferably aqueous ammonia with a concentration of 25 wt %-28 wt %.

The method for synthesizing a diaza-bridged compound provided in the present disclosure may also have the following characteristics that the post-treatment in step 2 or step ii includes the steps of: adding a extraction agent to the reaction mixture, extracting, taking an organic phase, washing with water, and recrystallizing to obtain compound 1, where the recrystallization agent used in the recrystallization step is a mixture of ethyl acetate and petroleum ether with a volume ratio of 1:(8-20), preferably a mixture of ethyl acetate and petroleum ether with a volume ratio of 1:(8-11); and the extraction agent includes any one or more of dichloromethane, toluene, ethyl ether, ethyl acetate, and tert-butyl methyl ether.

The method for synthesizing a diaza-bridged compound provided in the present disclosure may also have the following characteristic that the structural formula of compound 2 is

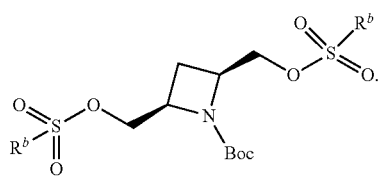

The method for synthesizing a diaza-bridged compound provided in the present disclosure may also have the following characteristics that the reaction formula for preparing compound 2 is:

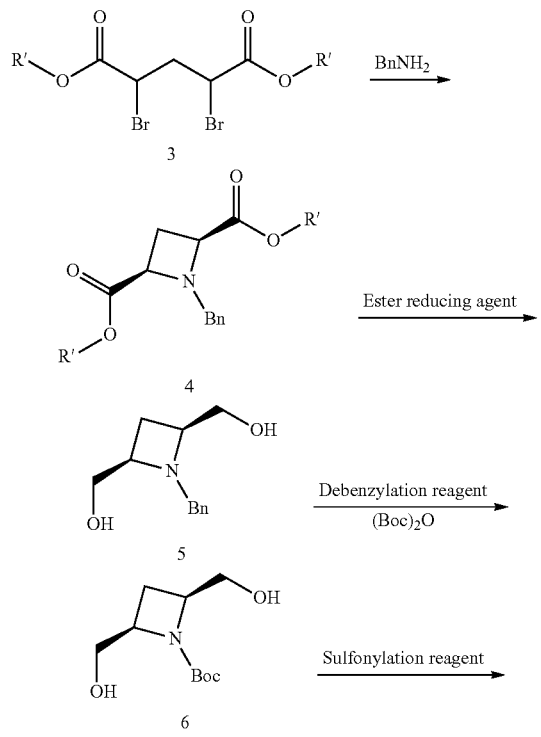

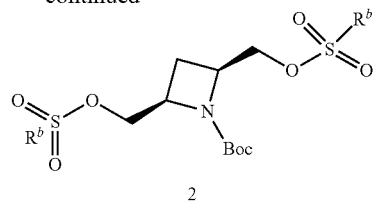

in the formula, R' is C1-C10 alkyl group,
and includes: step (1) of contacting compound 3 with benzylamine to obtain compound 4; step (2) of contacting of compound 4 with an ester reducing agent to obtain compound 5; step (3) of contacting compound 5 with a debenzylation reagent and (Boc)$_2$O sequentially or simultaneously to obtain compound 6; and step (4) of contacting compound 6 with a sulfonylation reagent to obtain compound 2, where the ester reducing agent is a reagent that can reduce the ester to an alcohol and can be composed of one or more compounds. In the present disclosure, the ester reducing agent is a reagent used to reduce an ester group to a hydroxyl group, which can be a single metal complex hydride (e.g., lithium aluminum hydride), a complex reducing agent consisting of a metal complex hydride with Lewis acid (e.g., sodium borohydride/aluminum trichloride), or a sodium metal. The debenzylation reagent is a reagent that removes a benzyl group from compound 5 without affecting other functional groups. The reagent can be composed of one compound, such as trifluoroacetic acid, DDQ (2,3-dichloro-5,6-dicyano-1,4-benzoquinone) and ammonium cerium nitrate, and a variety of compounds, such as H$_2$/Pd/C, Na/liquid ammonia/tert-butanol, etc. The sulfonylation reagent is a reagent that can react with compound 6 to form a sulfonate, which can be sulfonyl chloride (R$^b$SO$_2$Cl), sulfonyl bromide (R$^b$SO$_2$Br), sulfonic anhydride

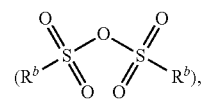

etc.

The method for synthesizing a diaza-bridged compound provided in the present disclosure may also have the following characteristics that in step (1) for preparing compound 2, compound 3 is contacted with benzylamine in the presence of an acid-binding agent, in which the acid-binding agent is any one of diisopropylethylamine or triethylamine, or a mixture thereof.

The method for synthesizing a diaza-bridged compound provided in the present disclosure may also have the following characteristics that in step (1) for preparing compound 2, the solvent is one or more of DMF, acetonitrile, toluene or tetrahydrofuran.

The method for synthesizing a diaza-bridged compound provided in the present disclosure may also have the following characteristics that after contacting compound 4 with the ester reducing agent, the step (1) for preparing compound 2 also includes a post-treatment procedure including adding a extraction agent into the reaction solution obtained by contacting compound 4 with the ester reducing agent, extracting, taking an organic phase, adding an acid gas to the organic phase, controlling the temperature as −10° C. to 10° C., stirring for 1 h-5 h, filtering, taking a solid, and drying to obtain compound 5.

The method for synthesizing a diaza-bridged compound provided in the present disclosure may also have the following characteristics that in step (1) for preparing compound 2, during the post-treatment procedure after contacting compound 4 with the ester reducing agent, the extraction agent is a mixture of toluene and water, preferably a mixture of toluene and water with a volume ratio of (1-3):(1-3), the volume ratio of the extraction agent to the initial reaction solution is 1:(0.8-2), and the acid gas is a hydrochloric acid gas.

The method for synthesizing a diaza-bridged compound provided in the present disclosure may also have the following characteristics that the structural formula of compound 2 is

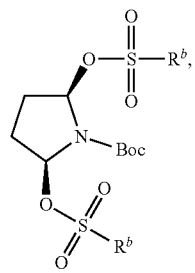

the reaction formula for preparing compound 2 is:

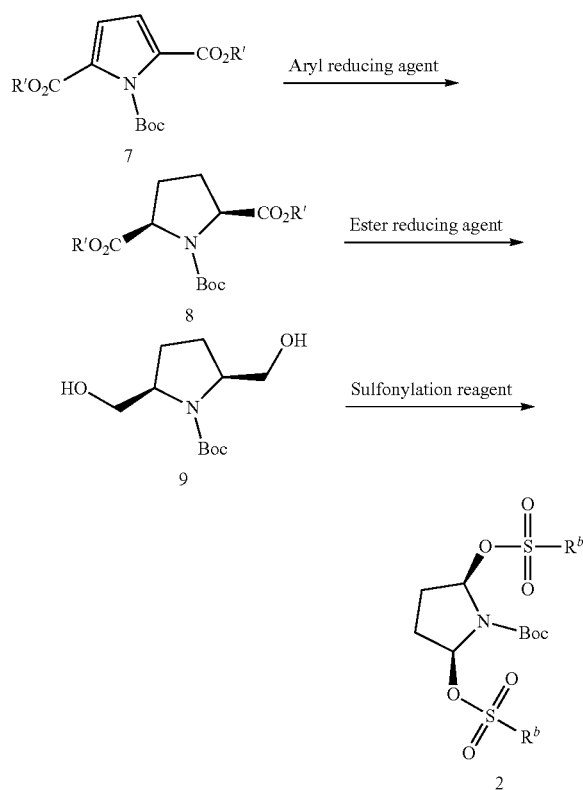

in the formula, R' is C1-C10 alkyl group,
and includes: step α of contacting compound 7 with an aryl reducing agent to obtain compound 8; step β of contacting of compound 8 with an ester reducing agent to obtain compound 9; and step γ of contacting compound 9 with a sulfonylation reagent to obtain compound 2, where the aryl reducing agent is a reagent used for catalytic hydrogenation reduction of pyrrole to pyrrolidine, such as $Pt/C/H_2$, $Cu/Al_2O_3$, ruthenium catalyst, nickel catalyst, etc.; the ester reducing agent is a reagent used to reduce an ester group to a hydroxyl group, which can be a single metal complex hydride (e.g., lithium aluminum hydride), a complex reducing agent consisting of a metal complex hydride with Lewis acid (e.g., sodium borohydride/aluminum trichloride), or a sodium metal; and the sulfonylation reagent is a reagent that can react with compound 9 to form a sulfonate, which can be sulfonyl chloride ($R^bSO_2Cl$), sulfonyl bromide ($R^bSO_2Br$), sulfonic anhydride

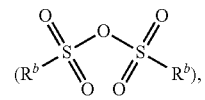

etc.

The diaza-bridged compound provided in the present disclosure may also have the following characteristics that in step a, compound 2 is contacted with $R^aNH_2$ or $R^aNH_2$ solution in a reaction medium, where the reaction medium is acetonitrile.

The diaza-bridged compound provided in the present disclosure may also have the following characteristics that the post-treatment in step b is a recrystallization, where the recrystallization of the compound includes the following steps: dissolving the crude product in solvent A, then adding solvent B, mixing evenly, standing at −50° C. to -10° C., precipitating crystal, and then filtering to obtain the target product; the solvent A is any one of carbon tetrachloride, chloroform, ethyl acetate, acetone, ethanol, methanol, dichloromethane, 1,2-dichloroethane, trichloroethylene, tetrahydrofuran, 2-methyltetrahydrofuran, ethyl formate, methyl acetate, isopropyl acetate, acetonitrile, propionitrile or carbon disulfide, and the solvent B is any one of petroleum ether, n-hexane, cyclohexane, benzene, diethyl ether, isopropyl ether, n-pentane, n-heptane, propyl ether, nitromethane or nitrobenzene.

The present disclosure also provides a diaza-bridged compound having the characteristics that the structural formula is as follows:

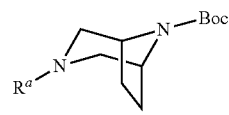

in the formula, $R^a$ is any one of 2-nitrobenzenesulfonyl, 4-nitrobenzenesulfonyl or 2,4-dinitrobenzenesulfonyl.

The diaza-bridged compound provided in the present disclosure may also have the following characteristic that in the formula, R is 2-nitrobenzenesulfonyl.

The diaza-bridged compound provided in the present disclosure may also have the following characteristic that the compound is obtained by recrystallization.

The diaza-bridged compound provided in the present disclosure may also have the following characteristics that the recrystallization of the compound includes the following steps: dissolving the crude product in solvent A, then adding solvent B, mixing evenly, standing at −50° C. to −10° C., precipitating crystal, and then filtering to obtain the target product; where the solvent A is any one of carbon tetrachloride, chloroform, ethyl acetate, acetone, ethanol, methanol, dichloromethane, 1,2-dichloroethane, trichloroethylene, tetrahydrofuran, 2-methyltetrahydrofuran, ethyl formate, methyl acetate, isopropyl acetate, acetonitrile, propionitrile or carbon disulfide, and the solvent B is any one of petroleum ether, n-hexane, cyclohexane, benzene, diethyl ether, isopropyl ether, n-pentane, n-heptane, propyl ether, nitromethane or nitrobenzene.

The diaza-bridged compound provided in the present disclosure may also have the following characteristics that the method for synthesizing the compound is as follows:

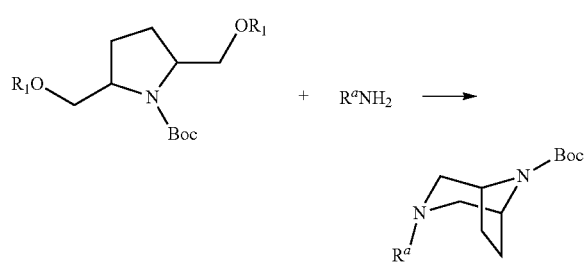

in the formula, $R^a$ is any one of 2-nitrobenzenesulfonyl, 4-nitrobenzenesulfonyl or 2,4-dinitrobenzenesulfonyl, and $R_1$ is an aryl, substituted aryl, alkyl or haloalkyl.

The diaza-bridged compound provided in the present disclosure may also have the following characteristics that the method for synthesizing the compound is as follows:

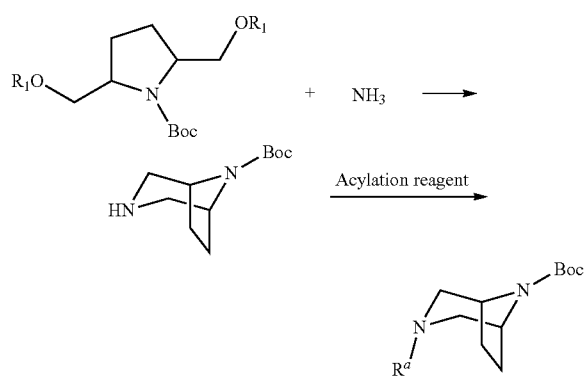

in the formula, $R_1$ is methylsulfonyl or p-tosyl, the acylation reagent is $R^aX$ or $R^aOR^a$, X is chlorine or bromine, and $R^a$ is any one of 2-nitrobenzenesulfonyl, 4-nitrobenzenesulfonyl or 2,4-dinitrobenzenesulfonyl.

The present disclosure also provides the use of the diaza-bridged compound in the preparation of medicines.

The use of the compound in the preparation of medicines provided in the present disclosure may also have the following characteristics that the medicine is Brepocitinib (the active ingredient is compound 1).

The use of the compound in the preparation of medicines provided in the present disclosure may also have the following characteristics that when $R^a$ is any one of 2-nitrobenzenesulfonyl, 4-nitrobenzenesulfonyl or 2,4-dinitrobenzenesulfonyl, the method for removing $R^a$ includes: dissolving the raw materials in a solvent, adding a alkali and a removal agent, stirring the reaction, washing with an acid, adjusting pH value to be alkaline, extracting with an organic solvent, and concentrating to obtain the target compound without $R^a$. Preferably, the solvent is DMF or acetonitrile, the alkali is any one or more of potassium carbonate, cesium carbonate, sodium carbonate, lithium hydroxide or DBU, and the removal agent is thiophenol or $HSCH_2COOH$ or 1-dodecanethiol. Preferably, the molar ratio of raw material, alkali and removal agent is 1:(1-3):(1-3).

Function and Effect of the Present Disclosure

According to the method for synthesizing a diaza-bridged compound involved in the present disclosure, since compound 2 and $RNH_2$ are used as raw materials, the present disclosure can not only effectively shorten the process flow and save process costs, but also improve the reaction yield to a certain extent.

According to the diaza-bridged compound involved in the present disclosure, since the two nitrogen atoms have two different protective groups, and the method for removing the two protective groups are different, that is, the process of removing one of the protective groups will not affect the other protective group, the diaza-bridged compound provided in the present disclosure is a multi-purpose intermediate that can be applied to the synthesis of multiple medicines.

Further, since the diaza-bridged compound

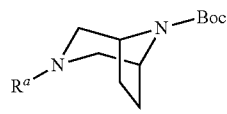

involved in the present disclosure has a higher melting point, is easy to recrystallize to get solid, and is not easy to form oil under high temperature, the diaza-bridged compound is suitable for long-distance transportation and long-term storage.

DETAILED DESCRIPTION

The content of the present disclosure is further illustrated below in combination with examples, however, the content claimed by the present disclosure is not limited to the following examples.

In order to make the technical means, creative features, accomplished purposes and efficacy achieved by the present disclosure easy to understand, the present disclosure is illustrated in detail below with the examples and the accompanying drawings.

In the following examples, each raw material is a commercially available product that is chemically pure, unless otherwise noted.

In the following examples, mass spectrometry data is obtained on a Waters Micromass LCT TOF mass spectrometer.

In the following examples, the melting point is determined by a commercially available melting point detector, which is not calibrated before use.

In the following examples, the following abbreviations may be referred to:
Boc: tert-butoxycarbonyl;
Ms: methylsulfonyl;
DMF: N,N-dimethylformamide;
THF: tetrahydrofuran;
DIPEA: diisopropylethylamine;
HATU: 1-[bis(dimethylamino)methylene]-1H-1,2,3-triazolo[4,5-b]pyridinium 3-oxide hexafluorophosphate.

Unless otherwise noted, the sources of raw materials in the following examples are commercially available and chemically pure.

Example 1

Synthesis of 6-(tert-butoxycarbonyl)-3,6-diazabicyclo[3.1.1]heptane

This example provides a method for synthesizing 6-(tert-butoxycarbonyl)-3,6-diazabicyclo[3.1.1]heptane (i.e., compound 1a), where the reaction formula is as follows:

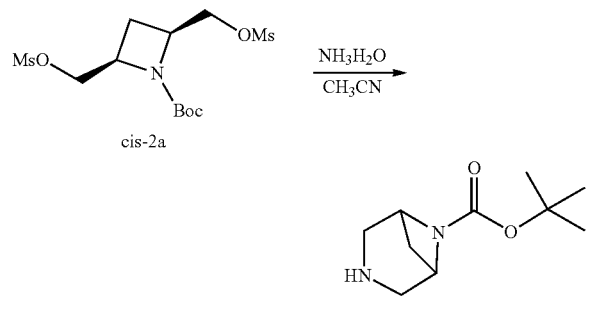

and the method specifically includes the following steps.

In step 1, 5 g (13.4 mmol, prepared by the method of example 5) compound cis-2a was added to 15 mL of acetonitrile, then 25 wt %-28 w t% of 50 mL concentrated ammonia (commercially available, not titrated before use) was added, heated to 70° C., and the reaction was stirred for 12 h to obtain a reaction solution.

In step 2, 20 mL of dichloromethane was added to the reaction solution, stirred, and extracted, the organic phase was taken and washed with water, and 100 mL of a mixture of ethyl acetate and petroleum ether with a volume ratio of 1:9 was added for recrystallization to obtain 1.9 g of compound 1a (i.e., 6-(tert-butoxycarbonyl)-3,6-diazabicyclo[3.1.1]heptane) as an off-white solid with a yield of 71.7%.

Figure 1:
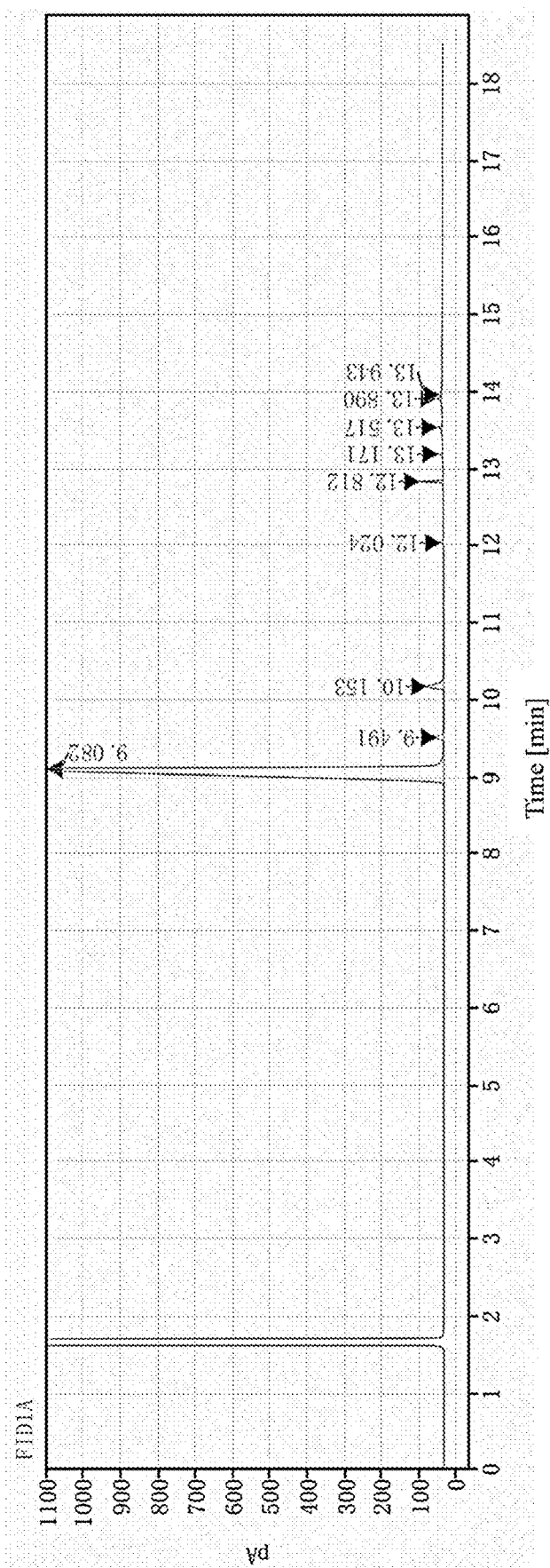
FIG. 1 is a graph showing the gas chromatography of 6-(tert-butyloxycarbonyl)-3,6-diazabicyclo[3.1.1]heptanein example 1 of the present disclosure.

FIG. 1 is a graph showing the gas chromatography of 6-(tert-butyloxycarbonyl)-3,6-diazabicyclo[3.1.1]heptane in example 1 of the present disclosure.

As shown in FIG. 1, the GC purity of compound 1 is 94.8% and could be introduced into the subsequent reaction without further purification.

TABLE 1

The GC data of FIG. 1

| Retention time [min] | Type | Peak width [min] | Peak area | Peak height | Peak area% |
|---|---|---|---|---|---|
| 9.082 | BV | 0.54 | 7406.37 | 1249.73 | 94.796 |
| 9.491 | VB | 0.43 | 73.99 | 16.81 | 0.947 |
| 10.153 | BB | 0.53 | 179.36 | 42.55 | 2.296 |
| 12.024 | BB | 0.18 | 14.11 | 4.7 | 0.181 |
| 12.812 | BB | 0.07 | 69.61 | 59.25 | 0.891 |
| 13.171 | BB | 0.21 | 22.11 | 9.41 | 0.283 |
| 13.517 | BB | 0.15 | 19.16 | 10.22 | 0.245 |
| 13.89 | BB | 0.05 | 13.41 | 10.83 | 0.172 |
| 13.943 | BB | 0.2 | 14.85 | 4.98 | 0.19 |
| — | — | — | Total 7812.98 | — | — |

Figure 2:
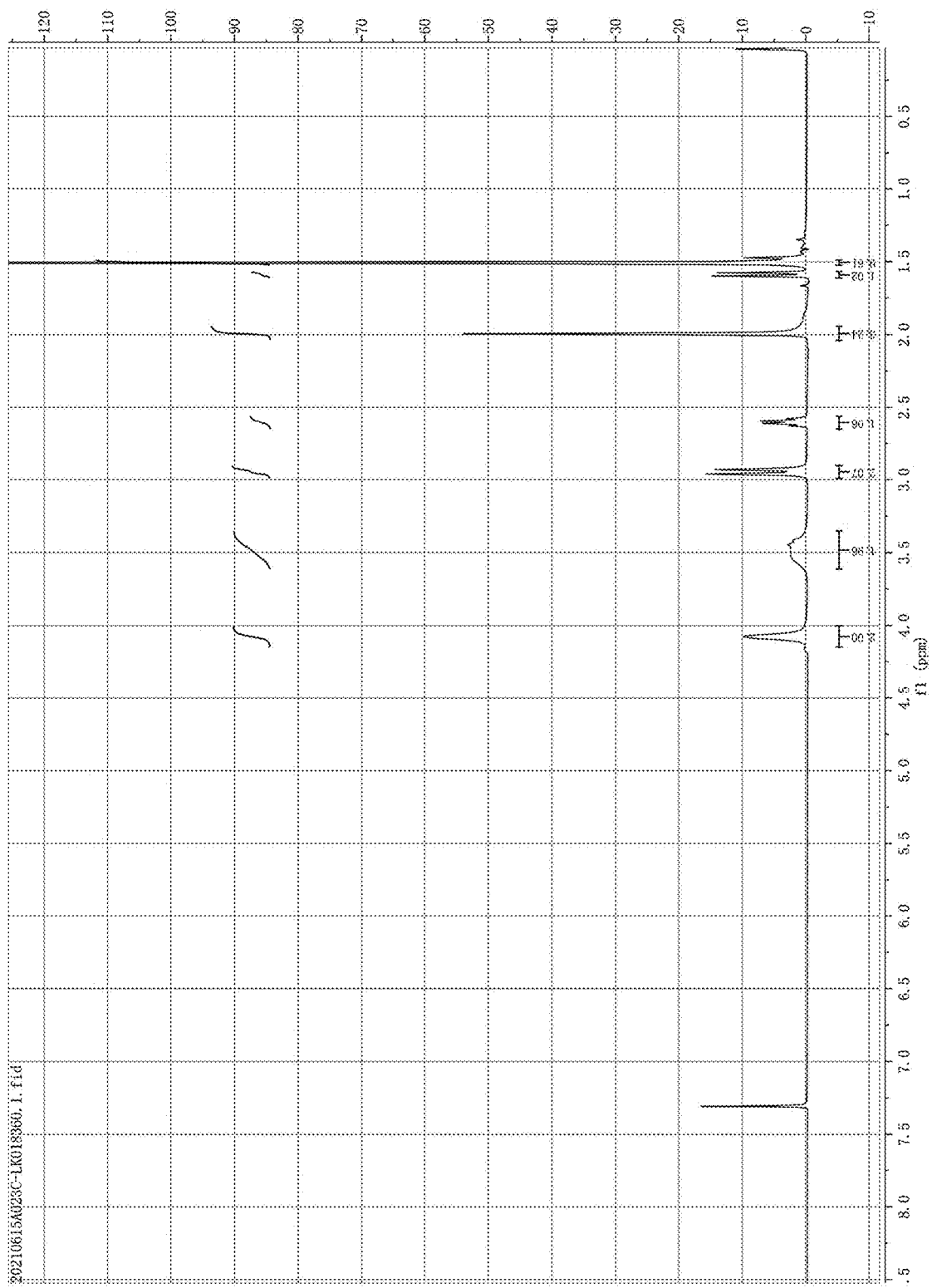
FIG. 2 is a graph showing the $^1H$ NMR spectrum of 6-(tert-butyloxycarbonyl)-3,6-diazabicyclo[3.1.1]heptane in example 1 of the present disclosure.

FIG. 2 is a graph showing the $^1$H NMR spectrum of 6-(tert-butyloxycarbonyl)-3,6-diazabicyclo[3.1.1]heptane in example 1 of the present disclosure.

As shown in FIG. 2, the $^1$H NMR spectrum of 6-(tert-butoxycarbonyl)-3,6-diazabicyclo[3.1.1]heptane (i.e., compound 1a) obtained in this example is consistent with that reported in the literature.

Example 2

Screening of Reaction Conditions

In this example, the reaction conditions were further screened on the basis of example 1, all the reaction conditions and operations were the same as in example 1 except for the conditions listed in the table, and the specific screened reaction conditions and corresponding reaction results are shown in Table 2.

TABLE 2

Table of reaction conditions screened for synthesizing compound 1a

| No. | Solvent | Reaction temperature | Yield | Purity |
|---|---|---|---|---|
| 1 | DMF | 70° C. | 65.5% | 83.4% |
| 2 | Acetonitrile | 30° C. | 51.2% | 92.8% |
| 3 | DMF | 30° C. | 45.1% | 81.4% |
| 4 | THF | 70° C. | 57.2% | 78.3% |
| 5 | THF | 30° C. | 43.3% | 72.4% |
| 6 | Methanol | 60° C. | Trace | — |

As shown in Table 2, when DMF, acetonitrile, and tetrahydrofuran are used as reaction solvents, the reactions proceed smoothly. However, when methanol is used as the solvent, the target product cannot be obtained, probably because the compound cis-2a is trans-esterified with methanol, and the product after the transesterification cannot react with aqueous ammonia, and thus the target product cannot be obtained.

In addition, the yield of compound 1 is significantly higher when the reaction temperature is 70° C. compared to 30 ° C. The purity of the product is solvent dependent to a certain extent, and when acetonitrile is chosen as the solvent, the purity of the product is significantly superior over the purity when DMF and THF are chosen as the solvent.

Example 3

Synthesis of cis-1-benzyl-2,4-diethoxycarbonylazetidine

This example provides a method for synthesizing cis-1-benzyl-2,4-diethoxycarbonylazetidine, where the reaction formula is as follows:

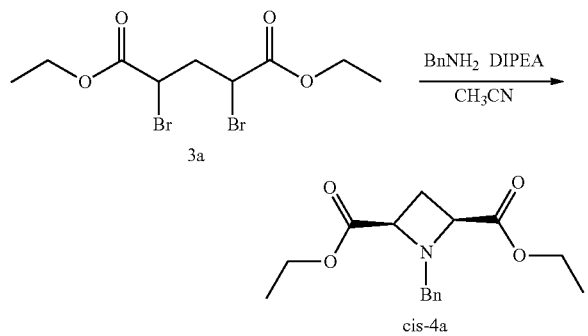

and the method specifically includes the following steps.

In step 1, 10.0 g (28.9 mmol,1 eq) diethyl 2,4-dibromoglutarate, 3.1 g (28.9 mmol,1 eq) benzylamine, 7.5 g (58.0 mmol,2 eq) diisopropylethylamine and 100 mL acetonitrile were added in a 250 mL reaction flask, heated to 85° C. and reacted under reflux for 5 h to obtain the reaction stock solution. At this time, the reaction stock solution was sampled and examined using HPLC, and the ratio of cis-product to trans-product in the reaction stock solution was 60.6%:12.3%, i.e., 4.9:1.

In step 2, the reaction stock solution was concentrated to 20 mL and extracted by adding an extraction agent consisting of 50 mL of toluene and 50 mL of water to obtain an organic phase. The organic phase was stirred while hydrochloric acid gas was introduced to pH 3 and the temperature was controlled at 0° C. During stirring, crystals were gradually precipitated from the organic phase. After the pH adjustment was completed, the temperature was continued to be controlled at 0° C. and the reaction was stirred for 2 h and filtered. The solid was taken and dried to obtain 5.82 g of the target product as a white solid with a yield of 69.2% and a liquid phase purity of 92.8%, which could be directly introduced to the next reaction step without further purification.

Figure 3:
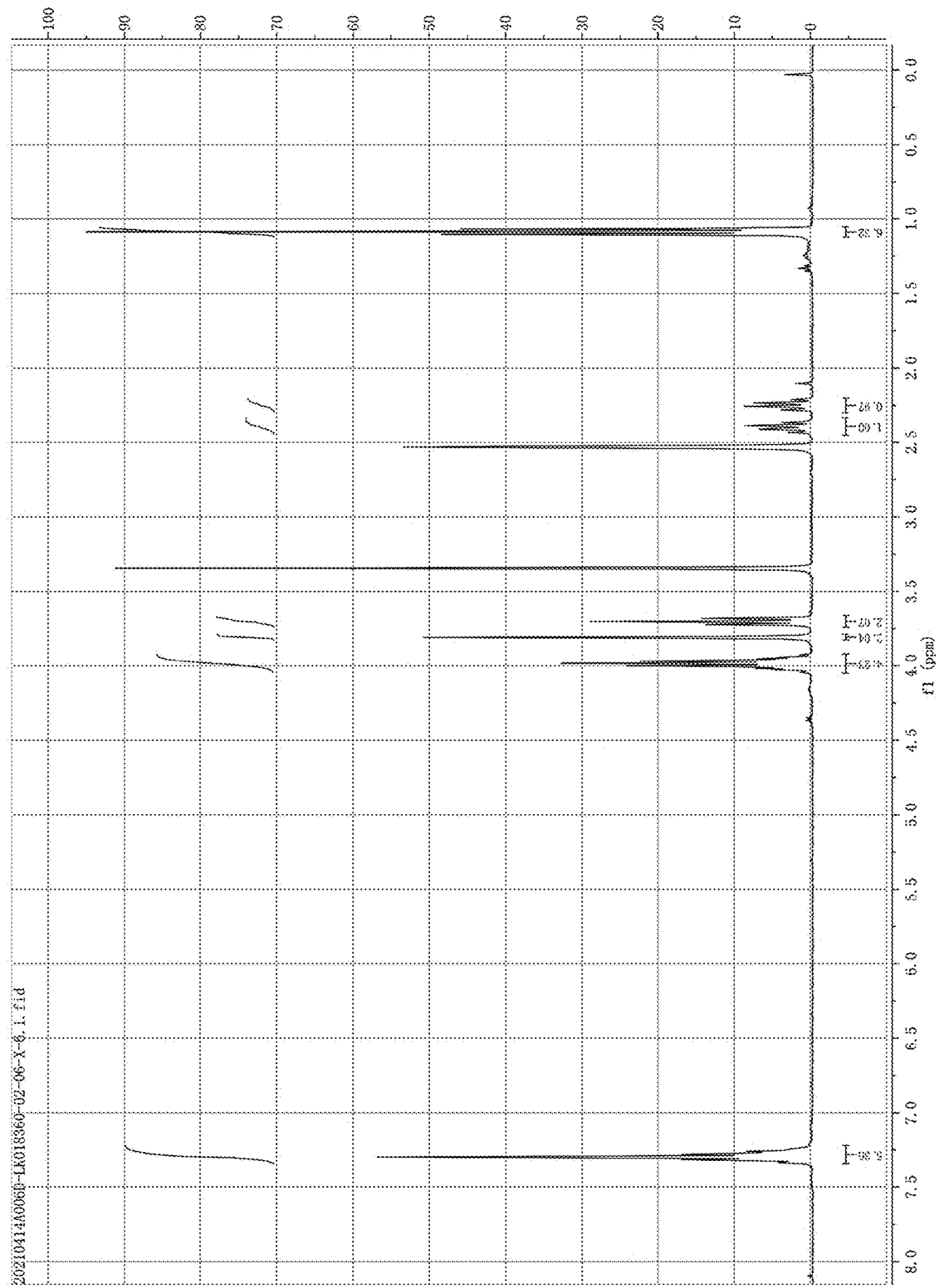
FIG. 3 is a graph showing the $^1H$ NMR spectrum of cis-1-benzyl-2,4-dialkoxycarbonylazetidinein example 3 of the present disclosure.

FIG. 3 is a graph showing the $^1$H NMR spectrum of cis-1-benzyl-2,4-dialkoxycarbonylazetidine in the example of the present disclosure.

As shown in FIG. 3, the spectrum is consistent with that of the cis-standard, and thus the product can be identified as cis-1-benzyl-2,4-diethoxycarbonylazetidine.

Comparative Example

Synthesis of cis-1-benzyl-2,4-diethoxycarbonylazetidine

This comparative example provides a method for synthesizing cis-1-benzyl-2,4-diethoxycarbonylazetidine, where the reaction formula is as follows:

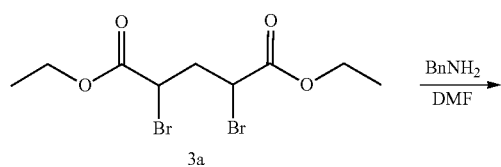

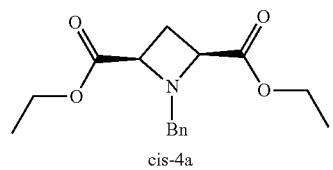

and the method specifically includes the following steps.

In step 1, 10.0 g (28.9 mmol,1 eq) diethyl 2,4-dibromoglutarate, 9.3g (86.7 mmol,3 eq) benzylamine and 100 mL of DMF were added in a 250 mL reaction flask, heated to 85° C. and reacted for 5 h to obtain the reaction stock solution. At this time, the reaction stock solution was sampled and examined using HPLC, and the ratio of cis-product to trans-product in the reaction stock solution was 31.6%: 37.6%, i.e., 1:0.84.

In step 2, the reaction stock solution was concentrated to 20 mL and extracted by adding an extraction agent consisting of 100 mL of dichloromethane and 100 mL of water to obtain an organic phase. Since the cis-trans ratio was too low for recrystallization, the organic phase was concentrated and separated by column chromatography to obtain 1.86 g of the target product as a yellow oily liquid with a yield of 22.1%.

Example 4

Screening of Reaction Conditions

In this example, the reaction conditions were further screened on the basis of example 3, and the specific screened reaction conditions and corresponding reaction results are shown in Table 3.

TABLE 3

Table of reaction conditions screened for synthesizing compound cis-4a

| No. | Acid-binding agent | Solvent | Cis:trans | Yield of cis-product |
|---|---|---|---|---|
| 1 | Diisopropylethylamine | DMF | 3.96:1 | 56.3% |
| 2 | Diisopropylethylamine | Toluene | 2.66:1 | 35.6% |
| 3 | Diisopropylethylamine | Tetrahydrofuran* | 2.92:1 | 37.5% |
| 4 | Triethylamine | Acetonitrile | 3.11:1 | 48.3% |

*Reaction temperature is 70° C. under reflux

As shown in Table 3, when diisopropylethylamine or triethylamine is chosen as the acid-binding agent, the cis-trans ratio of the product is higher than that when benzylamine is used as the acid-binding agent (see the comparative example); the solvent does not have a great influence on the cis-trans ratio, and the yields of the cis-products are all in the range of 30%-50%, among which the yields for DMF and acetonitrile can reach more than 40%.

Example 5

Synthesis of Compound cis-2a

This example provides a method for preparing compound cis-2a, where the reaction formula is as follows:

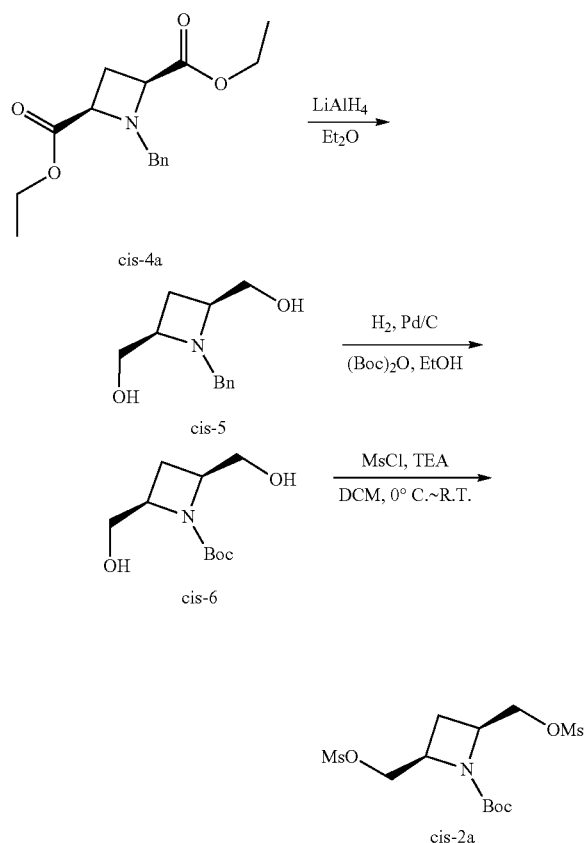

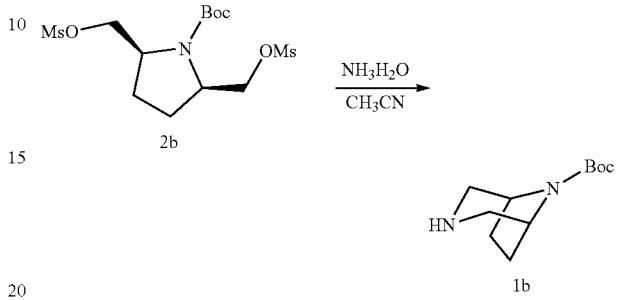

and the method specifically includes the following steps.

Step 1, 10 g (34.3 mmol, 1 eq, prepared by the method of example 3) of compound cis-4a was dissolved in 200 mL of anhydrous ether at 0° C., 2.74 g (72.0 mmol, 2.1 eq) of LiAlH₄ was added, and the reaction was quenched by adding 20 mL of water dropwise after 4 h at 0° C. The organic phase was taken, washed with saturated brine solution (100 mL×2), dried over anhydrous sodium sulfate and concentrated under reduced pressure to obtain 5.69 g of compound cis-5 with a yield of 80%.

In step 2, 5 g (24.1 mmol,1 eq) of compound cis-5 was dissolved in 120 mL of ethanol, 0.9 g (10%) of Pd/C was added, the gas was replaced, charged with hydrogen, and the reaction was stirred at room temperature for 36 h. 7.9 g (36.2 mmol,1.5 eq) of (Boc)₂O and 6.1 g (72.3 mmo,3 eq) of sodium bicarbonate were added. The reaction was continued at room temperature for 12 h, filtered over Celite and the filtrate was taken, dried over anhydrous sodium sulfate and concentrated reduced pressure to obtain 4.7 g of compound cis-6 with a yield of 90%.

In step 3, 4 g (18.4 mmol, 1 eq)of compound cis-6 was dissolved in 100 mL of dichloromethane, and 3.7 g (36.8 mmol, 2 eq) of triethylamine and 5.1 g (44.2 mmol, 2.4 eq) of MSCl were sequentially added dropwise under an ice-water bath, returned to room temperature naturally, reacted for 3 h, washed with 100 mL of water, and concentrated under reduced pressure, 150 mL of petroleum ether was added, slurried and filtered, and the solid was taken and dried at 60° C. for 6 h to obtain 5.9 g of compound cis-2a with a yield of 86%.

Example 6

Synthesis of compound tert-butyl 3,8-diazabicyclo[3.2.1]octane-8-carboxylate

This Example provides a method for synthesizing tert-butyl 3,8-diazabicyclo[3.2.1]octane-8-carboxylate, where the reaction formula is as follows:

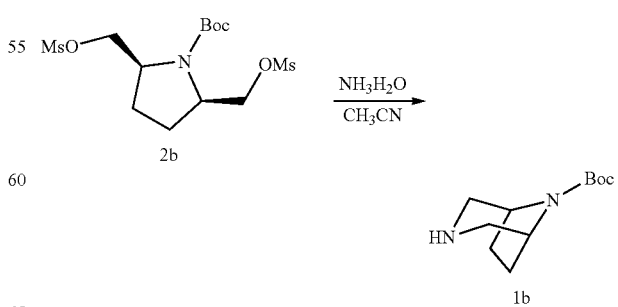

and the method specifically includes the following steps.

Step 1, 5 g (12.9 mmol, prepared by the method of example 9) of compound 2b was added to 15 mL of acetonitrile, then 25 wt %-28 wt % of 50 mL concentrated ammonia (commercially available, not titrated before use) was added, heated to 70° C., and the reaction was stirred for 12 h to obtain the reaction solution.

In step 2, 20 mL of dichloromethane was added to the reaction solution, stirred, extracted, and the organic phase was taken, washed with water, and 100 mL of a mixture of ethyl acetate and petroleum ether with a volume ratio of 1:9 was added for recrystallization to obtain 2.0 g of compound 1b (i.e., 3,8-diazabicyclo[3.2.1]octane tert-butyl 8-carboxylate) as an off-white solid with a yield of 72.9% and GC purity of 95.3%, which could be introduced to the subsequent reaction without further purification.

Figure 4:
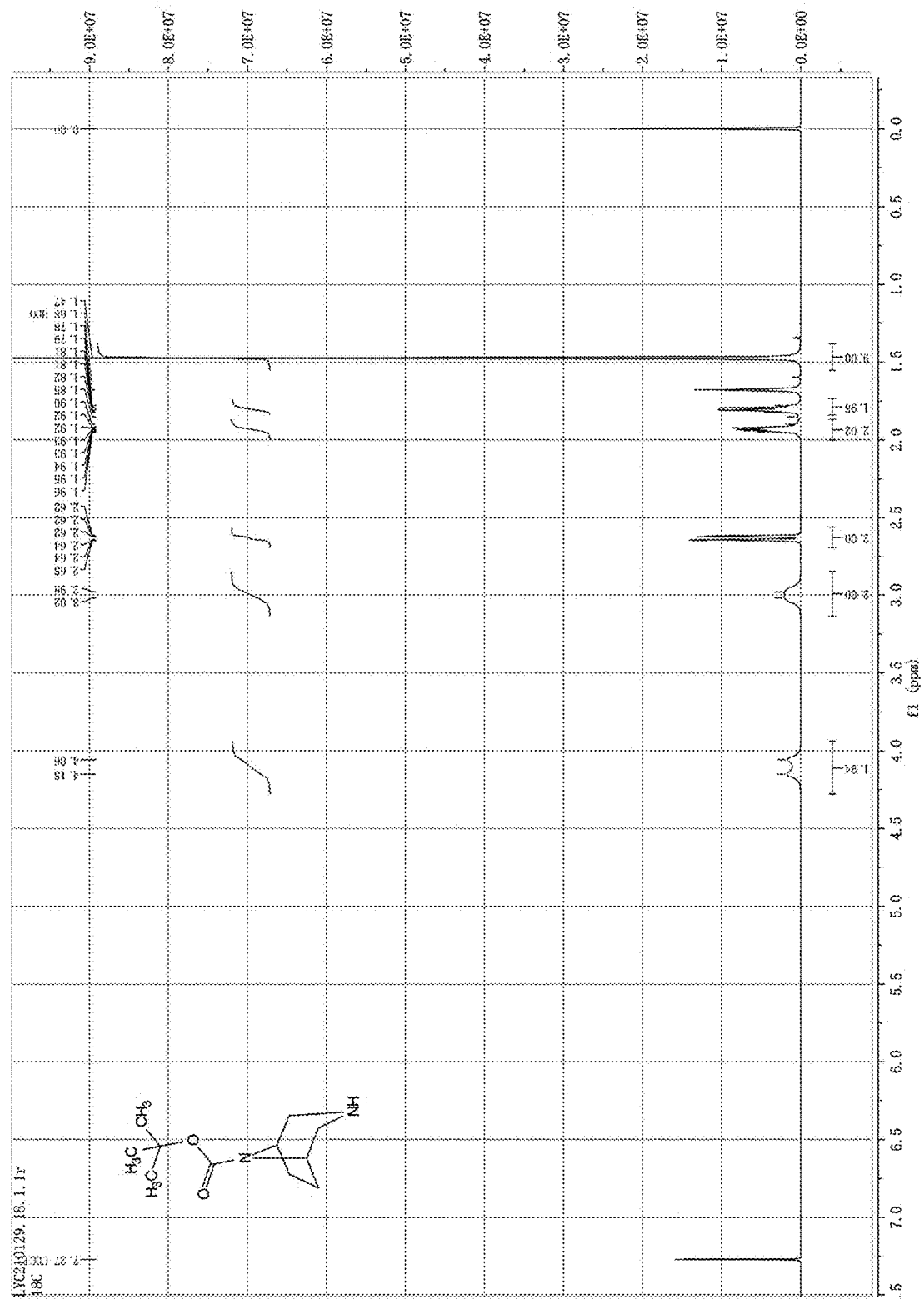
FIG. 4 is a graph showing the $^1H$ NMR spectrum of tert-butyl 3,8-diazabicyclo[3.2.1]octane-8-carboxylate in example 6 of the present disclosure.
Figure 5:
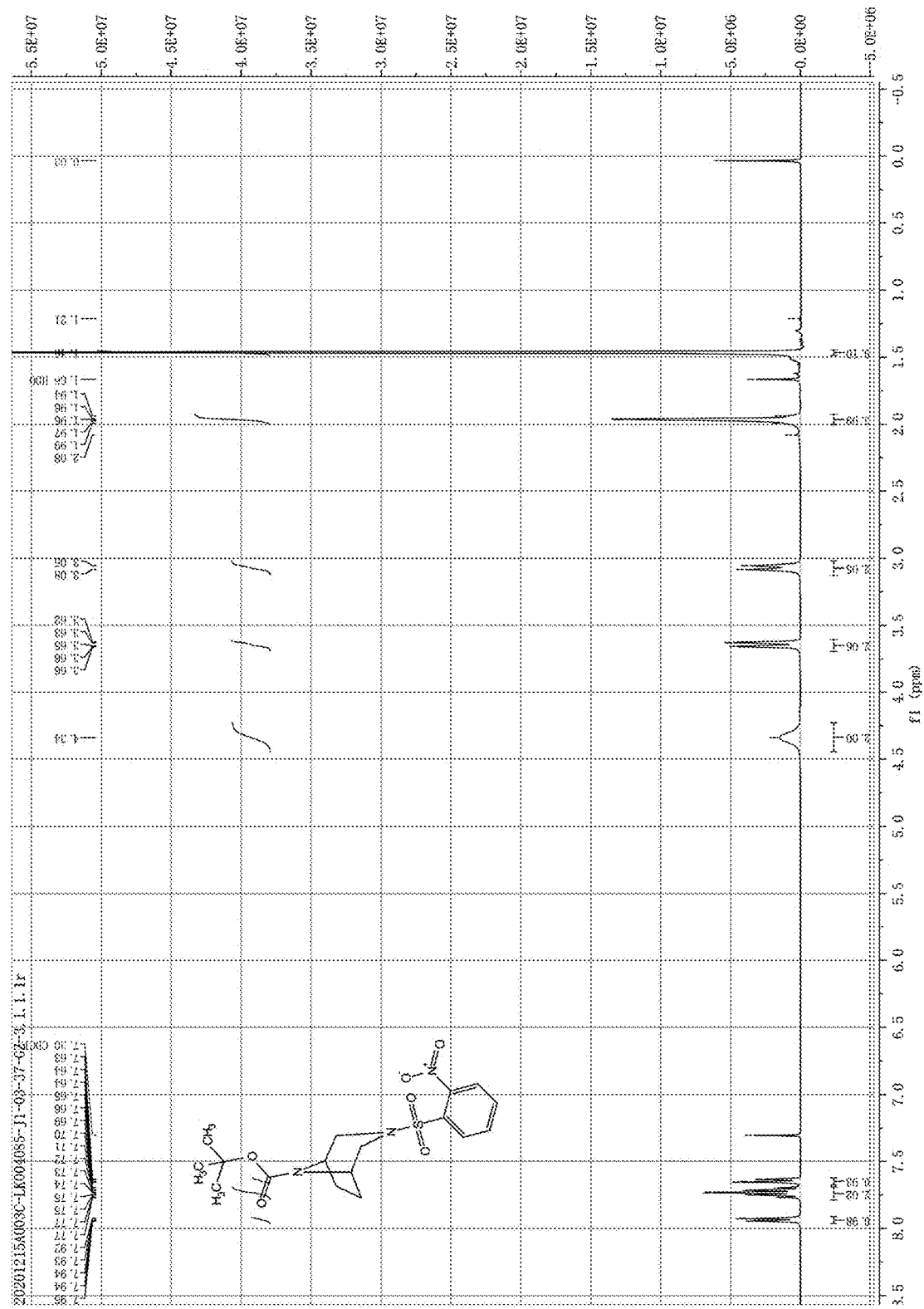
FIG. 5 is a graph showing the $^1H$ NMR spectrum of tert-butyl3,8-diazabicyclo[3.2.1]octane-3-(2-nitrobenzenesulfonyl)-8-carboxylate in example 10 of the present disclosure.

FIG. 4 is a graph showing the ¹H NMR spectrum of 6-(tert-Butoxycarbonyl)-3,6-diazabicyclo[3.1.1]heptane in example 6 of the present disclosure;

As shown in FIG. 4, the ¹H NMR spectrum of tert-butyl 3,8-diazabicyclo[3.2.1]octane-8-carboxylate (i.e., compound 1b) obtained in this example is consistent with that reported in the literature.

Example 7

Synthesis of compound tert-butyl 3,8-diazabicyclo[3.2.1]octane-8-carboxylate

This example provides a method for synthesizing tert-butyl 3,8-diazabicyclo [3.2.1]octane-8-carboxylate, where the reaction formula is as follows:

and the method specifically includes the following steps.

In step 1, 5 g (12.9 mmol, prepared by the method of example 9) of compound 2b was added to 65 mL of 0.5 M ammonia in tetrahydrofuran, heated to 70° C. under reflux, and the reaction was stirred for 12 h to obtain the reaction solution.

In step 2, 20 mL of dichloromethane was added to the reaction solution, stirred, extracted, and the organic phase was taken, washed with water, and 100 mL of a mixture of ethyl acetate and petroleum ether with a volume ratio of 1:9 was added for recrystallization to obtain 1.60 g of compound 1b (i.e., tert-butyl 3,8-diazabicyclo[3.2.1]octane-8-carboxylate) as an off-white solid with a yield of 58.4% and GC purity of 92.5%, which could be introduced to the subsequent reaction without further purification.

Example 8

In this example, the reaction conditions were further screened on the basis of example 6, all the reaction conditions and operations were the same as in example 6 except for the conditions listed in the table, and the specific screened reaction conditions and corresponding reaction results are shown in Table 4.

TABLE 4

Table of reaction conditions screened for synthesizing compound 1b

| No. | Solvent | Reaction temperature | Yield | Purity of liquid phase |
|---|---|---|---|---|
| 1 | DMF | 70° C. | 72.3% | 85.4% |
| 2 | Acetonitrile | 30° C. | 57.4% | 92.2% |
| 3 | DMF | 30° C. | 55.9% | 80.7% |
| 4 | THF | 70° C. | 67.2% | 74.5% |
| 5 | THF | 30° C. | 56.6% | 72.1% |
| 6 | Methanol | 60° C. | Trace | — |

As shown in Table 4, being similar to the synthesis of compound 1a, the reaction proceeds smoothly with DMF, acetonitrile or THF as the solvent. However, the reaction cannot proceed smoothly when methanol is used as the solvent. In addition, appropriately increasing the reaction temperature is beneficial to improve the yield and purity of the reaction.

Example 9

Synthesis of Compound 2b

This example provides a method for synthesizing of compound 2b, where the reaction formula is as follows:

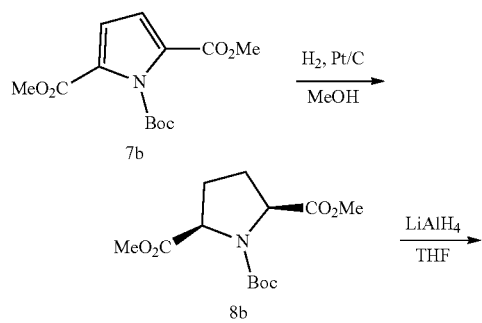

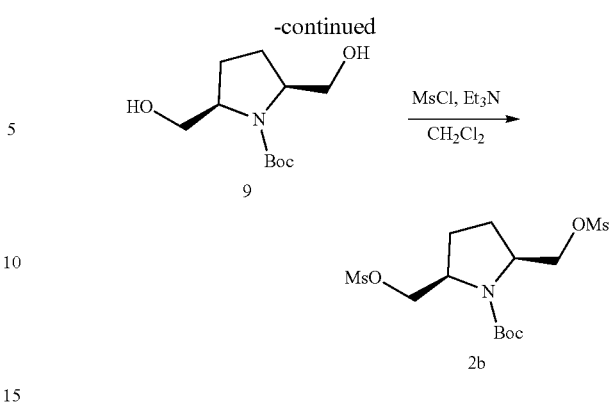

and the method specifically includes the following steps.

In step 1, 20 g (70.6 mmol, compound 7b was synthesized in this example by referring to the method reported in Donohoe T J, Headley C E, Cousins R , et al. Flexibility in the partial reduction of 2,5-disubstituted pyrroles: application to the synthesis of DMDP.[J]. Organic Letters, 2003, 5(7):999-1002.) of compound 7b was dissolved in 500 mL of methanol. Nitrogen was replaced at room temperature, 6 g (with Pt content of 10%) of Pt/C was added, and hydrogen was charged to a partial pressure of hydrogen to be 1 atm in the reaction system. The reaction was stirred for 8 h at room temperature, filtered using Celite, the filtrate was taken, and the solvent was evaporated to obtain 19.4 g of compound 8b with a yield of 95.6%, which was directly introduced to the next step without further purification.

In step 2, 4.8 g (126.3 mmol,2.0 eq) of LiAlH$_4$ was dissolved in 200 mL of anhydrous tetrahydrofuran solution at 0° C. to obtain a solution of LiAlH$_4$ in tetrahydrofuran, and 18 g (62.6 mmol,1.0 eq) of compound 8b was dissolved in 300 mL of anhydrous tetrahydrofuran to obtain a solution of compound 8b in tetrahydrofuran. The solution of compound 8b in tetrahydrofuran was added to the solution of LiAlH$_4$ in tetrahydrofuran under the protection of nitrogen, and the reaction was stirred at room temperature for 20 h. The reaction was quenched by adding 300 mL of saturated aqueous ammonium chloride solution and 150 mL of ethyl acetate and extracted. The organic phase was taken, washed with 1 M HCl aqueous solution (300 mL×3) and saturated brine solution (300 mL×1), respectively, and dried over anhydrous sodium sulfate. The solvent was evaporated under reduced pressure to obtain 12.4 g of compound 9 with a yield of 85.6%, which was directly introduced to the next step without further purification.

In step 3, 12 g (51.9 mmol,1 eq) of compound 9 was dissolved in 200 mL of anhydrous tetrahydrofuran, 13.1 g (129.8 mmol, 2.5 eq) of triethylamine was added, and 13.1 g (114.2 mmol, 2.2 eq) of methylsulfonyl chloride was added dropwise under an ice-water bath. The reaction was returned to room temperature naturally, stirred for 12 h, and sequentially washed with distilled water (300mL×1), 10 wt % citric acid aqueous solution (300mL×1) and saturated brine solution (300mL×1). The organic phase was taken, dried over anhydrous sodium sulfate, concentrated under reduced pressure, and recrystallized from chloroform/n-heptane system (v/v=1:10) to obtain 16.5 g of compound 2b with a yield of 82.1% and a liquid phase purity of 98.3%, which could be directly introduced to the subsequent reaction without further purification.

Example 10

Synthesis of Compound 1c

This example provides a method for synthesizing of compound 1c, where the reaction formula is as follows:

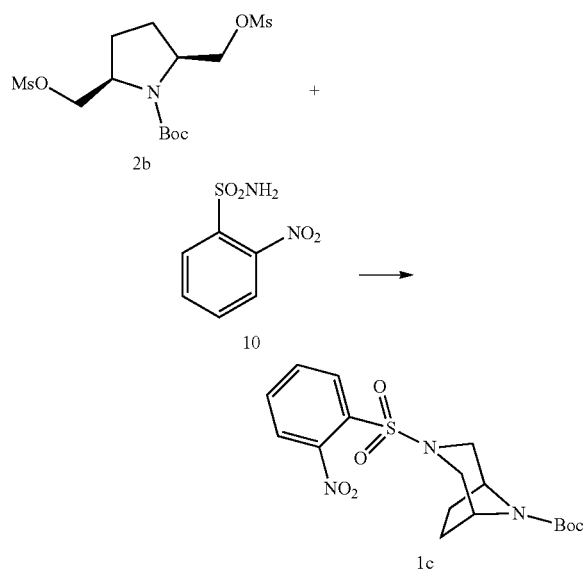

and the method specifically includes the following steps.

In step 1, 5 g (12.9 mmol, 1 eq) of compound 2b and 7.3 g (36.1 mmol, 2.8 eq) of compound 10 were dissolved in 50 mL of anhydrous acetonitrile. The reaction was performed at 85° C. for 8 h under reflux, returned to room temperature naturally, and washed twice with water. The organic phase was taken and the solvent was evaporated to obtain an oily product.

In step 2, ethyl acetate was added dropwise to the oily product obtained in step 1 until the oily product was completely dissolved in ethyl acetate, then 100 mL of propyl ether was added, mixed evenly, left to stand for 12 h at −20° C. and rapidly filtered by suction to obtain 4.25 g of crystals of compound 1c with a yield of 82.9%.

The $^1$H NMR spectrum of compound 1c prepared in this example is shown in FIG. 1.

The specific $^1$H NMR spectrum, mass spectrum, and melting point data are as follows.

$^1$H NMR (400 MHz, Chloroform-d) δ7.97-7.92 (m, 1H), 7.73 (pd, J=7.5, 1.8 Hz, 2H), 7.65 (dd, J=7.4, 1.8 Hz, 1H), 4.34 (s, 2H), 3.64 (dt, J=11.9, 1.7 Hz, 2H), 3.08 (d, J=11.5 Hz, 2H), 1.97 (t, J=2.8 Hz, 4H), 1.47 (s, 9H).

HRMS (ESI): m/z [M+Na]+calcd for $C_{17}H_{23}N_3O_6SNa$: 420.1205, found: 420.1209.

Mp: 185-187° C.

It can be seen that the melting point of compound 1c according to the present disclosure can reach 185-187° C., which is significantly higher than that of similar existing diaza-bridged compounds, easy to recrystallize to obtain a solid, less likely to form an oil at high temperature, and suitable for long-distance transportation as well as long-term storage.

Example 11

Synthesis of Compound 1c

This example provides another method for synthesizing of compound 1c, where the reaction formula is as follows:

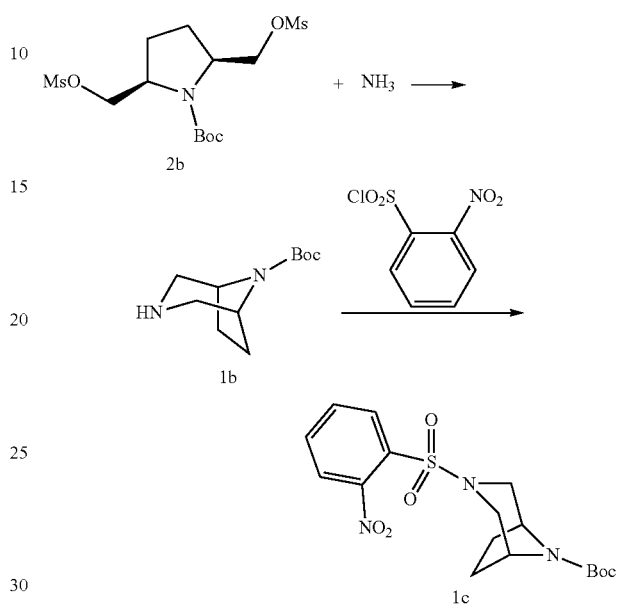

and the method includes the following step 1, step 2, step 3 and step 4.

In step 1, 5 g (12.9 mmol) of compound 2b was added to 15 mL of acetonitrile, then 25 wt %-28 wt % of 50 mL concentrated ammonia (commercially available, not titrated before use) was added, heated to 70° C. and the reaction was stirred for 12 h to obtain a reaction solution.

In step 2, 20 mL of dichloromethane was added to the reaction solution, stirred, extracted, and the organic phase was taken, washed with water, and 100 mL of a mixture of ethyl acetate and petroleum ether with a volume ratio of 1:9 was added for recrystallization to obtain 2.0 g of compound 1b (i.e., 3,8-diazabicyclo[3.2.1]octane tert-butyl 8-carboxylate) as an off-white solid with a single-step yield of 72.9% and GC purity of 95.3%, which could be introduced to the subsequent reaction without further purification.

In step 3, 5 g (23.6 mmol, 1 eq) of compound 1b was dissolved in 25 mL of anhydrous tetrahydrofuran, 2.86 g (28.3 mmol, 1.2 eq) of triethylamine was added, mixed evenly, then 5.74 g (26.0 mmol, 1.1 eq) of o-nitrobenzoyl chloride was added dropwise. The reaction was stirred for 3 h at room temperature, quenched by adding 30 mL of water, and washed twice with water. The organic phase was taken and the solvent was evaporated to obtain the oily product.

In step 4, ethyl acetate was added dropwise to the oily product obtained in step 3 until the oily product was completely dissolved in ethyl acetate, and then 100 mL of propyl ether was added. The reaction was mixed evenly, left to stand for 12 h at −20° C., and rapidly filtered by suction to obtain 8.67 g of crystals of compound 1c with a yield of 92.4%.

Example 12

Screening of Recrystallization Solvent

In this example, the solvent for the recrystallization of compound 1c was screened. 1 g of oily product obtained from the experiment conducted in the same pot according to the reaction steps recited in step 1 of example 1 was used for recrystallization in each group of experiments, and a mixed solvent recrystallization method was used for each group of experiments. Solvent A in Table 5 was a solvent with good solubility for the product (good solvent), and solvent B was a solvent with poor solubility for the product (poor solvent), the screening results are shown in Table 5.

TABLE 5

Screening table of recrystallization solvents

| No. | Solvent A | Solvent B | Properties of recrystallized product | Recrystallization yield |
|---|---|---|---|---|
| 1 | Tetrahydrofuran | Propyl ether | Semi-solid and semi-oily | — |
| 2 | Tetrahydrofuran | n-Hexane | Solid | 90.4% |
| 3 | 1,2-dichloroethane | n-Hexane | Oily liquid | — |
| 4 | Chloroform | Cyclohexane | Solid | 83.7% |
| 5 | Ethyl acetate | Isopropyl ether | Solid | 94.6% |
| 6 | Ethyl acetate | Propyl ether | Solid | 96.8% |

As can be seen from Table 5, compound 1c could not be recrystallized to obtain a solid when some solvents were chosen as recrystallizing agents, and the highest yield of recrystallization could be reached to about 95% when ethyl acetate was chosen as a good solvent and ether compounds were chosen as a poor solvent.

Example 13

Deprotection of Compound 1c

This example provides a method for removing the Boc group from compound 1c, where the reaction formula is as follows:

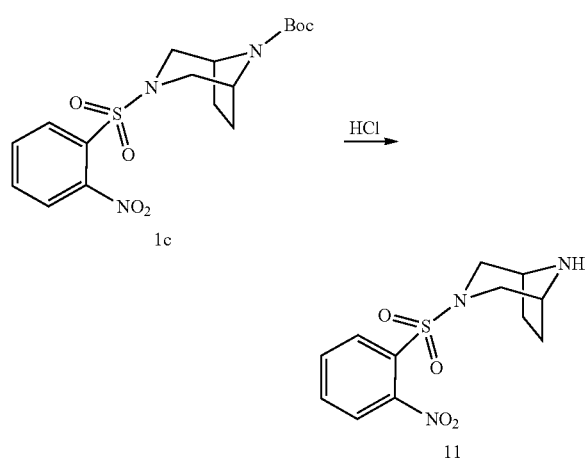

and the method includes the following step.

In this step, 5 g of compound 1c was added to a 100 mL solution of hydrochloric acid in methanol with a concentration of 3 mol/L. The reaction was stirred for 3 h at room temperature, the solvent was evaporated, 50 mL of deionized water was added, and 1 mol/L of sodium hydroxide was added dropwise until the pH value of the solution was 13. The mixture was extracted with dichloromethane (50 mL×2), the organic phase was combined and washed once with saturated brine solution. The solvent was evaporated to obtain 3.65 g of compound 11 as a yellow oily liquid at room temperature with a yield of 97.6%.

Example 14

Deprotection of Compound 1c

This example provides a method for removing the o-nitrobenzenesulfonyl group from compound 1c, where the reaction formula is as follows:

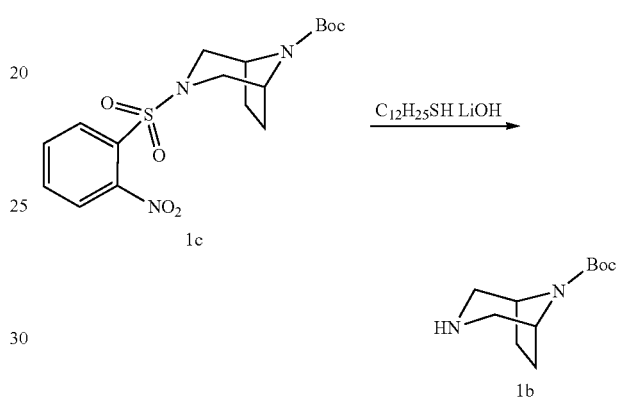

and the method includes the following step.

In this step, 5 g (12.6 mmol, 1 eq) of compound 1c was dissolved in 50 mL of DMF, 5.1 g (25.2 mol, 2 eq) of 1-dodecanethiol and 1.06 g (25.2 mmol, 2 eq) of lithium hydroxide monohydrate were added. The reaction was stirred for 2 h at room temperature, 100 mL of ethyl acetate was added and extracted with 1 mol/L aqueous hydrochloric acid (50 mL×2). The aqueous phase was combined, 1 mol/L sodium hydroxide was added dropwise to the aqueous phase until the pH value of the solution was 13 and extracted with dichloromethane (50 mL×2). The organic phase was combined, and the solvent was evaporated to obtain 2.26 g of compound 1b with a yield of 84.1%. Compound 1b was a light yellow solid at room temperature.

Example 15

Synthesis of Brepocitinib Intermediates

This example provides a method for synthesizing a Brepocitinib intermediate, where the reaction formula is as follows:

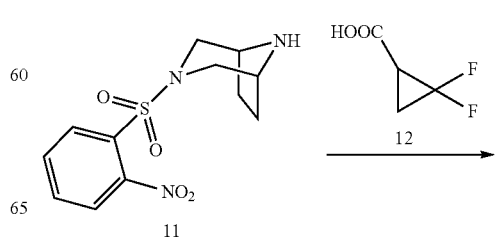

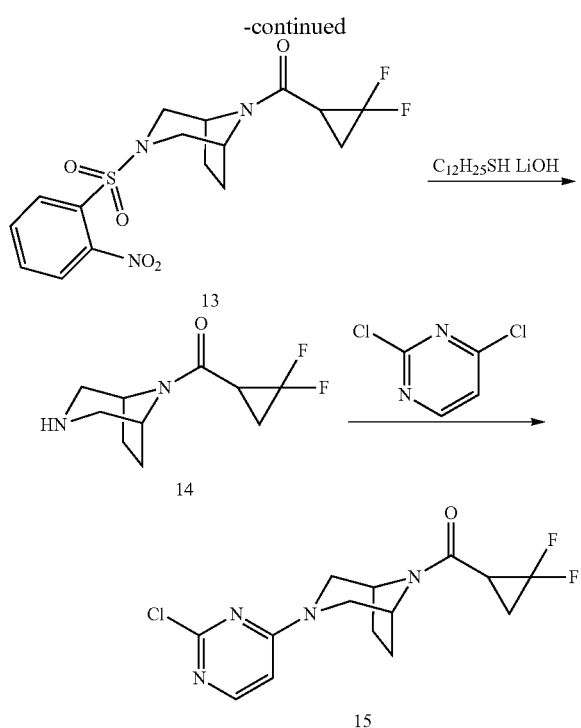

and the method includes the following step1, step 2, and step 3.

In step 1, 20 g (67.3 mmol, 1 eq) of compound 11, 16.4 g (134.6 mmol, 2 eq) of compound 12 and 20.4 g (201.9 mmol, 3 eq) of triethylamine were dispersed into 200 mL of DMF, then 30.7 g (80.8 mmol, 1.2 eq) of HATU was added, and the reaction was stirred at room temperature for 30 min, concentrated under reduced pressure, and purified with flash column chromatography to obtain 21.0 g of compound 13 with a yield of 77.7%.

In step 2, 20 g (49.8 mmol, 1 eq) of compound 13 was dissolved in 50 mL of DMF, 20.2 g (99.6 mmol, 2 eq) of 1-dodecanethiol and 4.17 g (99.6 mmol, 2 eq) of lithium hydroxide monohydrate were added, and the reaction was stirred at room temperature for 2 h. 100 mL of ethyl acetate was added and extracted using 1 mol/L of hydrochloric acid aqueous solution (50 mL×2). The aqueous phase was combined, 1 mol/L sodium hydroxide dropwise was added dropwise to the aqueous phase until the pH value of the solution was 13 and extracted with dichloromethane (50 mL×2). The aqueous phase was combined and the solvent was evaporated to obtain 8.89 g of compound 14 as a light yellow solid with a yield of 82.5%.

In step 3, 15 g (69.4 mmol, 1 eq) of compound 14 was dissolved in 500 mL of methanol under an ice-water bath, 11.4 g (76.3 mmol, 1.1 eq) of 2,4-dichloropyrimidine and 9.13 g (90.2 mmol, 1.3 eq) of triethylamine were added, and the reaction was naturally returned to room temperature and stirred for 12 h. The solvent was removed by concentration under reduced pressure and the residue was purified with flash column chromatography to obtain 18.3 g of compound 15 with a yield of 80.2%.

Function and Effect of the Examples

According to the synthesis method of diaza-bridged compounds covered by the above examples, since compound 2a or compound 2b and $NH_3$ are used as raw materials, the present disclosure can not only effectively shorten the process flow and save process costs, but also improve the reaction yield to a certain extent.

Further, since acetonitrile is used as the reaction solvent for the reaction between compound 2a or compound 2b and ammonia, the purity of the product can be effectively improved while ensuring the yield, thus allowing the product to be directly introduced to the next reaction step without further purification.

Further, since diisopropylethylamine or triethylamine is used as the acid-binding agent and DMF or acetonitrile is used as the solvent in the reaction for the preparation of cis-1-benzyl-2,4-dialkoxycarbonylazetidine (i.e., cis-4a), the present disclosure can obtain cis-1-benzyl-2,4-dialkoxycarbonylazetidine with a higher cis-trans ratio in high yield.

Further, the above examples also develop a crystallization method applicable to the diaza-bridged compound on the basis of obtaining a product with a high cis-trans ratio, which on the one hand can avoid column chromatography and simplify the post-treatment operation, making the industrialization of the product possible, and on the other hand, makes the final product in a solid state by crystallization, which is convenient for storage and transportation.

According to the diaza-bridged compound involved in the above examples, since the two nitrogen atoms have a Boc protecting group and an o-nitrobenzenesulfonyl group, respectively, and the method for removing the two protective groups are different, that is, the process of removing one of the protective groups will not affect the other protective group, the diaza-bridged compound provided in the present disclosure is a multi-purpose intermediate that can be applied to the synthesis of multiple medicines.

Further, since the diaza-bridged compound involved in the above examples has a higher melting point, is easy to recrystallize to get solid, and is not easy to form oil under high temperature, the diaza-bridged compound is suitable for long-distance transportation and long-term storage.

Further, since the protecting group at position 3 of the diaza-bridged compound involved in the above examples in o-nitrophenylsulfonyl, there is no need to use strong reducing reagents such as Pd/C, which are prone to break the bridge ring, when removing this protecting group, which has wider application in the synthesis of medicines.

Further, since the protecting group at position 3 in the diaza-bridged compounds involved in the above examples is o-nitrophenylsulfonyl, which is stable to strong acids and bases, more reagents are available for the modification of the nitrogen at position 8, which is suitable for the synthesis of some complex medicines or medicine intermediates.

The above embodiments are preferred examples according to the present disclosure and are not intended to limit the protection scope of the present disclosure.

Although the present disclosure has been disclosed as above with better examples, it is not intended to limit the present disclosure, and any person familiar with this technology can make various changes and modifications without departing from the spirit and scope of the present disclosure. Therefore, the protection scope of the present disclosure should be subject to what is defined in the claims.

What is claimed is:

1. A diaza-bridged compound having a structural formula of:

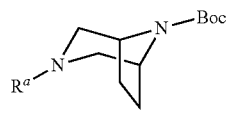

wherein in the formula, $R^a$ is any one of 2-nitrobenzenesulfonyl, 4-nitrobenzenesulfonyl, or 2,4-dinitrobenzenesulfonyl.

2. The diaza-bridged compound according to claim 1, wherein $R^a$ is 2-nitrobenzenesulfonyl.

3. The diaza-bridged compound according to claim 1, wherein the compound is obtained by recrystallization.

4. The diaza-bridged compound according to claim 3, wherein recrystallization of the compound comprises the following steps:

dissolving the diaza-bridged compound in solvent A, then adding solvent B, mixing evenly, precipitating a crystal at −50° C. to −10° C., and then filtering the crystal to obtain a recrystallized diaza-bridged compound, wherein:

the solvent A is any one of carbon tetrachloride, chloroform, ethyl acetate, acetone, ethanol, methanol, dichloromethane, 1,2-dichloroethane, trichloroethylene, tetrahydrofuran, 2-methyltetrahydrofuran, ethyl formate, methyl acetate, isopropyl acetate, acetonitrile, propionitrile, or carbon disulfide, and the solvent B is any one of petroleum ether, n-hexane, cyclohexane, benzene, diethyl ether, isopropyl ether, n-pentane, n-heptane, propyl ether, nitromethane, or nitrobenzene.

* * * * *